United States Patent [19]

Hu

[11] 4,159,894
[45] Jul. 3, 1979

[54] METHOD FOR DETERMINING FORMULATION AND CHEMICAL STRUCTURE OF MATERIALS BY IMPROVED PYROLYSIS GAS CHROMATOGRAPHY

[75] Inventor: John C. Hu, Renton, Wash.

[73] Assignee: The Boeing Company, Seattle, Wash.

[21] Appl. No.: 877,336

[22] Filed: Feb. 13, 1978

[51] Int. Cl.² .................... G01N 1/10; G01N 1/22
[52] U.S. Cl. ..................... 23/230 PC; 23/232 C; 23/230 M; 422/89; 422/78; 73/23.1; 73/422 GC
[58] Field of Search ........ 23/230 PC, 253 PC, 232 C; 73/23.1, 422 GC

[56] References Cited

U.S. PATENT DOCUMENTS

| | | | |
|---|---|---|---|
| 3,050,372 | 8/1962 | Scott | 23/230 PC |
| 3,088,808 | 5/1963 | Mandell, Jr. | 23/230 PC |
| 3,118,300 | 1/1964 | Jenkins | 73/422 GC X |
| 3,186,801 | 6/1965 | Hampton | 23/253 PC |
| 3,304,159 | 2/1967 | Hinsvark | 23/230 PC |
| 3,403,978 | 10/1968 | Favre | 23/230 R |
| 3,469,945 | 9/1969 | Delassus et al. | 23/230 PC |
| 3,518,059 | 6/1970 | Levy | 23/230 PC |
| 3,527,567 | 9/1970 | Philyaw et al. | 23/230 PC |
| 3,574,549 | 4/1971 | Eggertsen | 23/230 PC |
| 3,607,075 | 9/1971 | Wolf et al. | 23/230 PC |
| 3,661,527 | 5/1972 | Eggertsen et al. | 23/230 PC |
| 3,679,457 | 7/1972 | Gordon | 427/8 |
| 3,690,146 | 9/1972 | Hofmann | 23/254 E |
| 3,847,554 | 11/1974 | Su | 23/253 PC |
| 3,861,874 | 1/1975 | Krc | 23/253 PC |
| 3,880,587 | 4/1975 | Szakasits | 23/253 PC |
| 3,892,528 | 7/1975 | Fredericks | 23/253 PC |
| 3,898,041 | 8/1975 | Stephens et al. | 23/230 PC |
| 4,004,881 | 1/1977 | Ligon, Jr. | 23/253 PC X |
| 4,007,626 | 2/1977 | Roof et al. | 73/23.1 |

OTHER PUBLICATIONS

Hu, "Pyrolysis Gas Chromatog. Analysis of Rubbers and Other High Polymers", Analytical Chem., vol. 49, No. 4 (Apr. 1977), pp. 537–540.
Gast et al., "Polyester Amides from Linseed Oil for Protective Coatings", American Oil Chemists Society, vol. 43, No. 6, pp. 418–421.
Sansone et al., "Potential Hazard Associated with Removal of Needles from Septa in Inject. Ports of Gas Chromatograph", Anal. Chem., vol. 49, No. 4, (Apr. 1977), pp. 670–671.

Primary Examiner—R. E. Serwin
Attorney, Agent, or Firm—Christensen, O'Connor, Johnson & Kindness

[57] ABSTRACT

A material containing both volatile and nonvolatile components, such as a compounded high polymer, is analyzed using pyrolysis gas chromatography by directly inserting a sample into a sample injection chamber in contact with a flowing carrier gas stream upstream of a chromatographic column. Prior to inserting the sample, the carrier gas and the sample injection chamber are preheated to a temperature at which the volatile components in the sample will be rapidly vaporized. The temperature to which the injection chamber is preheated is, however, below that which will cause thermal degradation or pyrolysis of the polymeric component of the sample. After substantially all of the vaporizable component is removed from the sample and eluted from the chromatographic column, the polymeric component is pyrolyzed by heating it to a temperature sufficiently high to pyrolyze all of the pyrolyzable components of the sample. The pyrolysates are then carried to the chromatographic column by the carrier gas and eluted from the column. Both the volatile components and the pyrolysates are measured as they are eluted from the column and are graphically recorded to develop a chromatogram and a pyrogram, respectively. The chromatogram represents the specific formulation of the volatile components. The pyrogram represents the chemical structure of the nonvolatile (polymeric) components. Any residue remaining in the injection chamber after pyrolysis can be isolated for subsequent conventional analysis, if desired. Volatile, viscous liquids, such as oils, can also be analyzed by the first step of the procedure outlined above.

20 Claims, 20 Drawing Figures

METHOD FOR DETERMINING FORMULATION AND CHEMICAL STRUCTURE OF MATERIALS BY IMPROVED PYROLYSIS GAS CHROMATOGRAPHY

BACKGROUND OF THE INVENTION

This invention relates to thermal and pyrolytical analysis of samples having volatile components, nonvolatile, pyrolyzable components, and inorganic components by means of pyrolysis gas chromatography. More particularly, the invention relates to a simple, rapid, inexpensive and highly reproducible method for inserting a sample containing both volatile and nonvolatile, pyrolyzable components into a carrier gas stream flowing to a chromatographic column and for operating the associated chromatographic apparatus. In another aspect, the present invention relates to a method and apparatus for analyzing viscous, volatile liquids.

Pyrolysis is one of the oldest analytical techniques, dating back to the middle of the nineteenth century, still widely used by the analytical chemist today. The analytical techniques for pyrolytic studies of polymers has evolved from classical chemical methods, as disclosed for example by T. Midgley, Jr., et al., *Journal of the American Chemical Society*, Volume 51, page 1215 (1929), to instrumental methods. The modern instrumental methods employed in analytical studies are mass spectrometry, infrared spectroscopy, and gas chromatography. Gas chromatography, especially, has renewed the importance of pyrolysis as a tool in polymer analysis. Beginning in 1954, numerous studies on pyrolysis and gas chromatography were conducted, resulting in the publication of a large number of articles on pyrolysis gas chromatography, some of which are cited in "Pyrolysis Gas Chromatography Analysis of Rubbers and Other High Polymers", John Chih-An Hu, *Analytical Chemistry*, Volume 49, page 537, April, 1977.

The development of pyrolysis gas chromatography (PGC) as a precise analytical tool has been retarded by problems of interlab reproducibility and standardization. One approach to overcoming the prior difficulties in pyrolysis gas chromatography has been to use the Curie point pyrolyzer. Other researchers have suggested substituting photolysis for pyrolysis to improve reproducibility and standardization. Still others have suggested the use of sealed sample holders or the use of multicolumn chromatographic systems. Each of the prior art approaches has improved the performance of gas chromatographic methods but standardization and reproducibility are still significant problems to be overcome.

Variations in prior art PGC data have been attributed to several factors, such as variations in instrument design, pyrolyzer geometry, and temperature rise time. In addition to these factors, there are still other considerations that deserve special attention. When the sample to be pyrolyzed is a pure polymer or a compounded polymeric material with volatile constituents removed by extraction, reproducibility is relatively easy to achieve. However, complications usually arise when a compounded polymeric material in its original form, i.e., containing volatile materials, is analyzed. The prior art pyrolysis chromatogram of a compounded polymeric material in its original form is not a simple pyrogram but rather a compound pyrogram resulting from the inconsistent and nonreproducible superposition of a number of component chromatograms.

During pyrolysis, both vaporization and thermal degradation occur at the same time. If the injection port temperature of the chromatographic system approaches the boiling points of some but not all of the volatile constituents of a sample, some of the volatile constituents will be vaporized as soon as the sample is introduced into the chromatographic apparatus. Those vapors will then be developed into a chromatogram. The remaining volatile constituents will be vaporized by the initial heating of the pyrolysis probe heater after the probe heater is energized. The remaining vapors develop a chromatogram different from the vapors initially released. Moreover, part of the vapors released upon energization of the probe heater may undergo vapor phase pyrolysis to produce a pyrogram different from the chromatogram that would otherwise be produced from the nonpyrolyzed vapors. Finally, the nonvolatile constituent is pyrolyzed to develop yet a different pyrogram. All of the chromatograms and pyrograms thus developed, except the pyrogram of the nonvolatile constituent itself, are subject to variations depending on injection port temperature and post-injection waiting period (the time interval between sample insertion and pyrolysis). A logical prior art solution to these problems is to eliminate the volatile components by solvent extraction. Solvent extraction, however, is time consuming, requires large sample sizes and does not meet the quality assurance criteria of simplicity, rapidity, and inexpensiveness.

Accordingly, it is a broad object of the present invention to provide a standardized method of using pyrolysis gas chromatography that will yield reproducible results on a wide variety of materials when employing diverse kinds of chromatographic systems. It is another object of the present invention to provide analytical methods for testing materials such as commercial compounded polymeric materials, for example, rubbers and other high polymers, that meet the standards required by the aerospace industry quality assurance guidelines and provisions. It is a further object of the present invention to provide analytical methods utilizing pyrolysis gas chromatography that are accurate, rapid, simple, and inexpensive.

Another problem associated with prior art PGC is the introduction of oils and other viscous liquids into the gas chromatographic equipment. Previously, samples of oils and other viscous liquids are introduced into the injection port of the gas chromatographic equipment by one of three basic procedures. First the sample is dissolved in a suitable solvent to make a solution. The solution is thereafter injected by means of a syringe into the injection port through a septum covering the injection port. A second method is to place the sample in a glass tube and seal both ends of the tube. The sealed tube is then placed in a special apparatus, conventionally called a "solid sample injector" and thereafter is inserted through the injection port. The solid sample injector includes an apparatus for breaking the glass tube after it is in the injection chamber by pushing a plunger located on the exterior of the injection chamber. A third method for introducing oils and other viscous liquids into an injection chamber is to inject oils directly into the injection chamber through a septum covering the injection port by means of a syringe.

Both of the first and second procedures outlined above are tedious and time consuming. The third procedure is not workable under normal conditions because the viscous oils and other viscous liquids can hardly be drawn into the syringe in the first place and thereafter ejected from the syringe because of their viscosity. Moreover, at the elevated pressures employed in the gas chromatographic analysis of viscous liquids, normally on the order of 40 p.s.i.g., volatile liquid components tend to leak back through the septum, causing not only a loss of sample but perhaps precipitating serious health problems in the operator of the chromatographic equipment should any of the volatile components be toxic. See Sansone, E. B., *Analytical Chemistry*, Volume 49, page 670, April 1977.

Accordingly, it is another object of the present invention to provide a method of introducing viscous liquid samples into a gas chromatography apparatus that does not require sample preparation, that is simple and rapid to effect, that provides accurate and reproducible chromatograms, that requires a very small amount of sample, that is inexpensive and that is relatively safe for the operator of the chromatographic equipment.

SUMMARY OF THE INVENTION

In accordance with the foregoing objects, and other objects that will become apparent to one of ordinary skill upon reading the following specification, one aspect of the present invention provides a method for separating and analyzing a sample containing at least one volatile component and at least one nonvolatile, pyrolyzable component. First, a flow of carrier gas is established through a sample injection chamber. The carrier ga is then routed to and through a chromatographic column. The carrier gas is preheated prior to the time it flows past the injection chamber to a predetermined temperature that is sufficiently high to vaporize the volatile component in the sample, but which is below the pyrolysis temperature of the nonvolatile, pyrolyzable component. The sample to be analyzed is inserted into the injection chamber through which the preheated carrier gas is flowing. The volatile component is then allowed to vaporize and pass to the chromatographic column with the carrier gas. After substantially all of the volatile component has been vaporized from the sample and eluted from the column, the sample is heated to a second predetermined temperature at which the nonvolatile component is pyrolyzed to its gaseous reaction products, i.e., to its pyrolysates. The pyrolysates are allowed to pass to the chromatographic column with the carrier gas and thereafter to be eluted from the column. A chromatogram is prepared as the volatile component passes through the chromatographic column and a separate pyrogram is prepared as the pyrolysates pass through the chromatographic column.

The foregoing method of introducing a sample containing both volatile and nonvolatile components is very simple to effect and provides stable, reproducible results with a variety of chromatographic equipment under a variety of conditions. Moreover, the chromatogram and pyrogram can be developed in accordance with the present invention in a matter of minutes, contrasted with the extraction methods known in the prior art of separating the volatile components from the sample, which normally take days to complete. The method of the present invention is very simple since the sample can be mounted on a conventional pyrolysis probe. The probe is then inserted into the injection chamber through which the preheated carrier gas flow has been established, whereupon the volatile component of the sample will vaporize. After the volatile component of the sample has been vaporized and eluted, the heating element of the pyrolysis probe can be energized to pyrolyze the nonvolatile component in the sample. The pyrolysates are then carried to and eluted from the chromatographic column by the carrier gas. The method of the present invention is also highly cost effective, since conventional apparatus can be employed to effect the method and because the labor requirement and turn around time for analysis of various samples is relatively low.

In accordance with another aspect of the present invention, a volatile viscous liquid is inserted into the injection chamber of a gas chromatographic apparatus by first placing the liquid in a capillary tube. The capillary tube is then retentativelypositioned on a probe sized to be inserted through an injection port into the injection chamber of the chromatographic apparatus. The capillary tube, for example, can be positioned within the spiral coiled filaments of a conventional pyrolysis probe or a similar coil with no electrical connection. Prior to inserting the probe holding the capillary tube into the injection chamber, a flow of carrier gas is established through the injection chamber. The carrier gas is preheated prior to flowing through the chamber to a temperature sufficiently high to vaporize the liquid. The probe, including the liquid-containing capillary tube, is inserted through the injection port into the injection chamber. Thereafter, the preheated carrier gas volatilizes the viscous liquid and carries it to and elutes its components from the chromatographic column.

This method of inserting a viscous liquid sample into a chromatographic apparatus is very simple and easy to effect. Use of the capillary tube allows very precise control over the size of the sample placed in the injection chamber, yet no sample is lost during insertion through the injection port. A complete chromatogram of the viscous liquid can be obtained with the present invention in a very short time, since all of the sample components are vaporized substantially simultaneously. Moreover, the syringe and septum required by the prior art methods are eliminated, along with the tedious procedure associated with injecting a sample through the injection port with a syringe. And, importantly, the health hazard problems associated with syringe injection are virtually eliminated.

BRIEF DESCRIPTION OF THE DRAWINGS

A better understanding of the present invention can be derived by reading the ensuing specification in conjunction with the accompanying drawings, wherein:

FIGS. 5A and 5B are chromatograms and pyrograms of two different nitrile rubbers, while

FIG. 6A is a chromatogram andd pyrogram of a butyl rubber while

DETAILED DESCRIPTION

Figure 1:
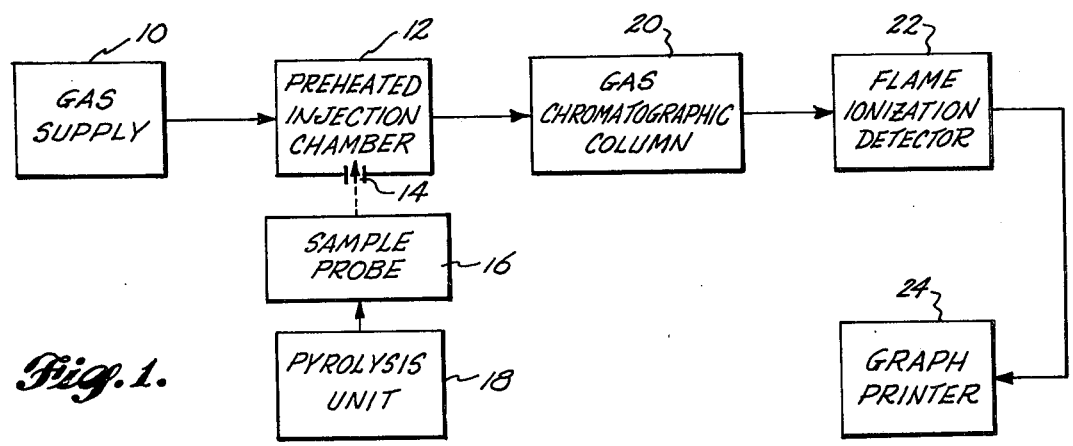
FIG. 1 is a block diagram of a conventional chromatographic apparatus with which the methods of the present invention can be employed.

FIG. 1 is provided as an overview of a gas chromatographic apparatus with which pyrolysis gas chromatography is conducted in accordance with the present invention. Carrier gas is supplied from a pressurized source 10. Carrier gas is normally stored in pressure containers and supplied to the remainder of the apparatus via suitable pressure conduits. The carrier gas employed with the present invention can be any of those conventionally used with pyrolysis gas chromatography, for example, helium. In accordance with the present invention, the carrier gas is continuously supplied to the injection chamber 12 during analysis. The carrier gas can be heated in a separate heat exchanger prior to entering the injection chamber or can be heated merely by exposure to the heated walls of the injection chamber. The injection chamber carries an injection port 14 to be described in more detail below. A sample probe 16 carrying a sample to be analyzed is inserted into the injection chamber 12 through the injection port 14. The pyrolysis 18 is electrically coupled to the sample probe 16. As will be described in more detail below, the sample probe usable with the present invention can be any of a variety of conventional types having a heating element in contact with or surrounding the sample to be analyzed. Gasses produced from the sample in the injection chamber are conducted via suitable conduits in the chromatographic apparatus to the gas chromatographic column 20. Various gas components from the sample to be analyzed are eluted at various rates in the gas chromatographic column 20 and are discharged from the column at various times, depending upon the component itself, the carrier gas, the flow rate of the carrier gas, and the packing in the column. Preferably, as the components are eluted from the column, they are passed through a conventional quantitative detector 22, which produces a signal representative of the gas components flowing therethrough. Although the embodiment of the invention described herein employs a flame ionization detector as detector 22, it is to be understood that any of a variety of conventional detectors can be employed as well. The signal produced by the detector 22 is fed to a graph printer 24 of conventional design. The graph printer conditions the signal received from the flame ionization detector to drive a stylus and print a graph on advancing graph paper indicative of the signal produced by the flame ionization detector.

Materials that can be analyzed in accordance with one method of the present invention are those which contain at least one volatile component and at least one nonvolatile, pyrolyzable component. Examples of materials that fall within this category are polymer compositions, natural and synthetic rubber compositions, adhesives, sealants, and paints or enamels, all of which in commercial form normally contain volatile components as well as at least one nonvolatile, natural or synthetic polymer. Examples of such volatile components include plasticizers, extenders, accelerators, retarders and antioxidants. A wide variety of other materials that can be analyzed in accordance with the present invention will be readily recognized by one of ordinary skill.

Figure 2:
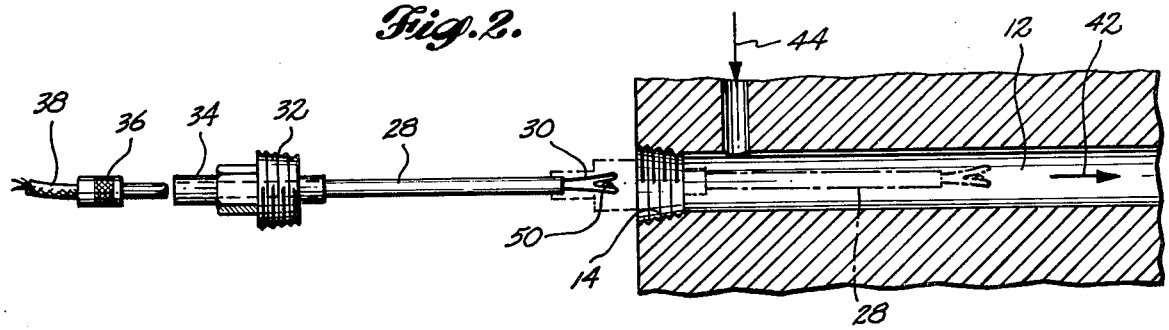
FIG. 2 is a somewhat simplified diagram of a conventional pyrolysis probe having a ribbon heating element and the associated conventional injection port and injection chamber as used in accordance with the present invention.
Figure 2A:
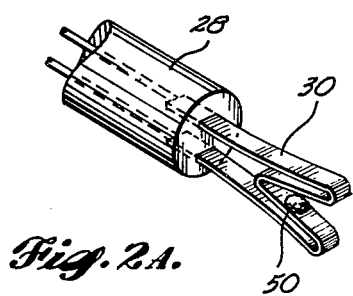
FIG. 2A is an enlarged isometric view of the tip of the injection probe and ribbon heating element of FIG. 2 holding a sample in accordance with the present invention.

Referring to FIGS. 2 and 2A, a sample 50 of a material to be analyzed is first positioned on the heating element 30 of a conventional pyrolysis probe 16. The pyrolysis probe 16 comprises a shank 28 having a threaded coupling 32 which is sized to threadably engage the injection port 14 leading to the injection chamber 12. The end of the pyrolysis probe 16 opposite the heating element 30 carries a female electrical coupling 34 that can be connected to a male coupling 36, which is in turn electrically connected to a power lead 38. The power lead 38 is connected to the power supply in the pyrolysis unit 18 (FIG. 1).

Still referring to FIGS. 2 and 2A, the carrier gas flows through an inlet channel in the direction of the arrow 44, through the injection chamber 12, and from the injection chamber to the chromatographic column in the direction of arrow 42. The carrier gas is preheated to a predetermined temperature prior to the time it comes into contact with the sample. The carrier gas can be heated in a separate heat exchanger upstream from the injection chamber 12, or can be heated by contact with the walls of the injection chamber that have been heated by suitable means to a temperature at or slightly above the desired predetermined temperature. The predetermined temperature is preferably above the temperature at which the volatile component in the sample will be volatilized in a reasonable period of time and below a temperature at which the nonvolatile component will pyrolyze.

Once the sample 50 is positioned on the probe heating element 30, the plug (not shown) normally closing the injection port 14 is removed and the shank 28 of the pyrolysis probe 16 and the sample are inserted into the injection chamber. Normally, the pyrolysis probe 16 carries a seal (not shown), such as an O-ring, that seals the region between the end of the probe and the injection port once the probe is fully inserted through the port. Other conventional sealing techniques can also be employed to prevent contaminants from entering the port after the probe is inserted. Once the sample is in the chamber, the preheated carrier gas causes the volatile component or components in the sample to volatilize. The volatile components are carried by the carrier gas to and through the chromatographic column 20 (FIG. 1). When the volatile components are eluted from the chromatographic column, they travel to the flame ionization detector 22. The signal from the flame ionization detector then provides a peak, or an input signal, to the graph record or printer 24 which in turn prints a chromatogram which can be reproduced with a very high degree of accuracy when the method of the present invention is followed.

After the volatile component or components are vaporized from the sample and eluted from the gas chromatographic column, the chromatogram is in essence complete. Thereafter, the pyrolysis unit 18 is activated to energize the heating element 30 on the pyrolysis probe 16 and heat the element to a temperature that will cause the pyrolyzable component or components in the sample to react and produce pyrolysis reaction products (pyrolysates). The pyrolysates are carried by the carrier gas to the chromatographic column 20 where they are differentially eluted in a conventional manner. As the pyrolysis products are eluted from the column, they are again conducted to the flame ionization detector 22 in a conventional manner. The signal from the flame ionization detector is again fed to the graph printer 24 to print a pyrogram that is separate from the chromatogram. The pyrogram is very accurately reproducible when the foregoing method is followed.

If desired, any nonvolatile, nonpyrolyzable inorganic materials remaining on the heating element of the pyrolysis probe can be withdrawn from the injection chamber and analyzed separately by conventional analytical chemistry techniques.

Each of the three component groups in the sample, that is the volatile components, the nonvolatile pyrolyzable components, and the inorganic components, can be analyzed separately and sequentially in accordance with the present invention. The volatile components are first separated as just described by merely inserting the pyrolysis probe containing the sample into the preheated injection chamber. Within a very few seconds after the pyrolysis probe is loaded into the injection chamber, the temperature of sample is raised sufficiently so that the volatile components are removed from the rest of the sample by vaporization and immediately enter the chromatographic column as a slug. This first step, when all the conditions of operating the column are the same, produces a characteristic, reproducible chromatogram which is a fingerprint of the chemical composition of the volatile group of components of the sample. Chromatograms of the same material from repeated runs are essentially identical. By comparison, when a sample of a material analyzed in accordance with the present invention is also analyzed by conventional solvent extraction techniques, the resultant chromatogram obtained from the liquid mixture extracted by conventional techniques is virtually identical to the chromatogram obtained by the method of the present invention. By contrast, however, the method of the present invention requires only minutes to perform while the prior art extraction technique consumes substantially more time and effort.

After the chromatogram has been completely developed, usually on the order of fifteen to thirty minutes, the second step of the method is initiated simply by energizing the heating element of the pyrolysis probe. When the pyrolysis probe is heated, the pyrolysates are very quickly produced and again enter the chromatographic column as a slug. The program produced from the eluted pyrolysates is reproducible and characteristic of the nonvolatile, pyrolyzable component. The pyrogram produced in accordance with the present invention thus provides a fingerprint of the chemical composition of the pyrolysates which are derived specifically from the pyrolyzable components of the sample. After the pyrogram has been completely developed, usually taking on the order of from fifteen to thirty minutes, the pyrolysis probe that holds the remains of the sample is withdrawn from the injection port. The inorganic components of the original sample that remain on the pyrolysis probe heating element are available for a complete analysis if desired.

One of ordinary skill in the art will realize that the peaks appearing on the chromatograms and pyrograms can be specifically identified by chemical composition using available techniques. For quality assurance pusposes, however, it is not necessary to identify the chemical structure of each peak on the chromatogram or pyrogram, but merely to recognize that a specific pattern is obtained. Material identification can be empirically accomplished for quality assurance purposes by comparing the fingerprint (or characteristic chromatogram or pyrogram) of a sample of unknown composition with a fingerprint of a known standard. If desired, the conventional methods such as retention parameters, gas chromatography-mass spectrometry, or vapor phase pyrolysis gas chromatography can be utilized to qualitatively determine chemical structure of each peak.

The temperature to which the injection chamber and the carrier gas passing through the injection chamber are heated can range from 100° C. to 400° C. Most preferably, however, a temperature in the range of 250° C. to 300° C. is employed. The temperature may be varied depending upon the particular sample being analyzed. The temperature of 270° C. is one at which most of the volatile components present in rubbers, paints, and other polymer formulations will volatilize while the nonvolatile components of those materials will remain substantially stable. It has been found that the polymeric components of all samples on which the present invention has been employed will remain stable for the relatively short period during which the initial chromatogram of the volatile materials is developed. It has been found that polymers used in most rubber compounds are stable below 300° C., thus allowing the predetermined temperature of the carrier gas and injection chamber to be raised as high as 300° C. Thus, depending on the nature of nonvolatile, pyrolyzable material other than rubber compounds, the injection chamber and carrier gas can be maintained at a temperature as high as or higher than 300° C. The thermal stability of materials other than those for which a specific example is given herein can be easily determined by conventional methods such as thermal gravimetric analysis. For example, thermal gravimetric analyses on materials such as silicone, neoprene, nitrile, butyl, poly(vinyl chloride) and ethylene-propylene-terpolymers indicate that such materials are thermally stable below 300° C.

It has also been found that volatile, high boiling additives in samples to be analyzed in accordance with the present invention can be removed from the sample at temperatures substantially lower than their boiling points. For example, heavy esters that have boiling points up to 400° C. under atmospheric pressure can be removed from a sample at temperatures on the order of 200° C. to 240° C. Likewise, the fluoroesters of camphoric acid with a molecular weight of 1228 and a boiling point of 460° have been volatilized at temperatures on the order of 325° C. within a fourteen minute time period. When such high boiling components are present in a sample analyzed in accordance with the present invention, the pyrogram resulting from a compounded sample, for example a compounded butyl rubber, is the same as a pure butyl rubber gum. (See Examples V through IX below.) Thus, such high boiling additives present in the samples are removed completely at the preferred temperature of 270° C. before the pyrolysis step of the invention is initiated.

The pyrolysis temperature preferred for use with the present invention is approximately 1000° C. The time period during which this temperature is maintained can be on the order of fifteen seconds. Invariable pyrolysis conditions are not necessary with the present invention to obtain good results with different samples. A pyrolysis temperature sufficiently high to produce pyrolysates that will be eluted in the gas chromatographic column is all that is necessary. Temperatures ranging from 600° C. up to 1500° C. or higher can therefore be employed with the present invention without affecting the accuracy of reproducibility of the results.

The time span between insertion of the sample into the chamber and the initiation of pyrolysis is usually governed by the time that is required to develop a complete chromatogram of the volatile component or components of the sample. For polymer compositions, rubber compositions and paint formulations, it has been found that a complete chromatogram can be developed in a period of about fifteen to twenty-five minutes when the temperature of the carrier gas in the injection chamber is on the order of 270° C. (assuming the chromatographic column is initially at a temperature of 100° C. and is programmed to increase in temperature to 300° C. at a rate of 20° C. per minute). At these temperatures, the volatile components are almost immediately vaporized and all enter the chromatographic column as a slug. Similarly, once pyrolysis is initiated, the pyrolysates are generated rather quickly and enter the chromatographic column as a slug. For materials such as the rubber, polymer or paint compositions previously mentioned, and for a pyrolysis temperature on the order of 1000° C., it has been found that a complete pyrogram is developed in on the order of fifteen to twenty-five minutes, depending upon the retention time in the chromatographic column of the pyrolystate that produces the last peak in the pyrogram.

As will be illustrated in the Examples that follow, other than for the method of separating the components of the sample and the manner in which the sample is inserted into the injection chamber, standard procedures are followed for regulating the gas supply, for passing the carrier gas and the sample components through the chromatographic column, and for detecting the presence of the various components with a conventional detector, such as a flame ionization detector. Likewise, the graph printer that converts the electrical signal from the detector to a visible graph is a conventional laboratory apparatus. It has been found, however, that it may be necessary to adjust the vertical attenuation of the graph prior to pyrolysis of the sample as the quantity of pyrolysates may not be as high in the sample as the volatile materials. Thus it is preferred that the attenuation setting on the printer be adjusted to provide a vertical scale on the graph that is equal for both the chromatogram and the pyrogram.

The specific Examples set forth hereafter are intended to be illustrative of the invention disclosed in the specification. The Examples are intended to teach one of ordinary skill how to use the invention to analyze and produce chromatograms and pyrograms for specific samples of material. It is to be understood that the invention has much broader application than the specific procedures set forth in the Examples and therefore, the Examples are not to be construed as delimiting in any way the broad concepts disclosed herein.

APPARATUS USED IN THE EXAMPLES:

A Hewlett-Packard FM 810 gas chromatograph with a flame ionization detector and a Hewlett-Packard FM 80 pyrolysis unit were employed to produce the chromatograms and pyrograms illustrated in FIGS. 3 through 8 and 11 and 12. The FM 810 gas chromatograph includes an integral graph recorder or printer. For the odd shaped samples analyzed in Examples I through IX, a platinum ribbon pyrolysis probe similar to that illustrated in FIGS. 2 and 2A was used to hold the sample and insert it into the injection chamber. For the procedures of Examples X through XII, a platinum spiral coil pyrolysis probe was used. For liquid samples, very small samples, powder samples or conductive samples, a glass capillary tube similar to that illustrated in conjunction with FIGS. 9 and 10 and described in additional detail later in the specification can be employed to hold the sample and position it in the spiral coil. A convenient range of sample weight for analysis is between about 2 and 8 mg. However, the sample size can be substantially smaller without affecting the results of the analysis. The sample size is not limited by the capability of the chromatographic apparatus to detect small amounts of material, but only by the operator's ability to obtain and place a tiny sample firmly in the probe. Only the current reading (amperage) of the pyrolysis unit was monitored as an indication of the temperature of the ribbon or coil on the pyrolysis probe. The temperature/amperage relationship for determining the temperature of the ribbon probe is calibrated by the manufacturer. Although it is known that the resistance of a platinum coil will change with age, the temperature drop accompanying the resistance change with a constant current is not detrimental to the procedures described herein. That is, the temperature changes will not affect the pyrogram pattern.

The columns used for all examples utilized SE-30 (methyl silicone) packing. Such columns are, for example, available from Applied Science Laboratories, Inc., State College Pennsylvania or from Hewlett-Packard Corporation, one of the sales offices of which is located at Bellefield Office Park, Bellevue, Wash. 98004. Variations in column size and percentage loading of the packing will not alter the pyrogram pattern, but may change the retention time of the gaseous components in the column to a certain degree. For all experiments, the column temperature was programmed. Helium was used as the carrier gas and flow rates were set at 30 ml/minute for a 0.318 cm column and 60 ml/minute for a 0.635 cm column. A flame ionization detector having a range of $10^3$ power was employed to detect the presence of the components eluted from the column. The flame ionization detector was chosen because of its high sensitivity to organic molecules and because of its insensitivity to air, water and carbon dioxide. For all Examples, the temperature of the injection chamber and the carrier gas entering the chamber was set at 270° C.

Operating Procedure

For the solid samples containing both volatile and nonvolatile components, a thin sliver of sample (for insertion into a spiral coil probe or a capillary tube held by a spiral coil probe) or a flate sample (for the ribbon probe) was cut from the material to be analyzed and loaded onto the pyrolysis probe. When the probe was ready for loading into the injection chamber, the conventional, threaded septum retainer was removed from the injection port and the loaded probe quickly inserted through the port into the injection chamber. The injection probe was threadably engaged onto the injection port and sealed in a conventional manner. The time when the port was reclosed and sealed with the pyrolysis probe was noted as the zero time of the chromatogram. During the first step of the analysis, when the volatile materials were being vaporized from the sample, the chromatographic column temperature was programmed to increase in temperature at a rate of 20° C. per minute from 100° C. to 300° C. Once the temperature of the column reached 300° C., it was held at 300° C. until the chromatogram was completely developed. After the completion of the chromatogram of the volatile components, the temperature of the column was reduced to 30° C. and the nonvolatile components were pyrolyzed at a predetermined amperage and duration. For Examples I through X, the temperature of the platinum ribbon was held at approximately 900° C. to 1100° C. for 5 to 15 seconds by maintaining an amperage across the probe in the range of 10 to 14 amps. For optimum reproducibility, energization of the ribbon at 12 amps for 15 seconds is preferred. The time when the current to the probe was initiated was noted as the zero time for the pyrogram. For analysis of the pyrolysates, the column temperature was programmed to increase at a rate of 20° C. per minute from a beginning temperature of 30° C. to a final temperature of 300° C., and was thereafter held at 300° C. until the pyrogram was completely developed. Thereafter, the pyrolysis probe which held the sample residue (any inorganic material present in the sample) was withdrawn from the injection port. The sample residue was collected for subsequent analysis. The probe was cleaned simply by pushing the pyrolysis button for a second or two while it was held in the air.

EXAMPLE I

A new silicone rubber seal was analyzed by cutting a small sliver from the seal and placing it on the pyrolysis probe. The operating procedure outlined above was then initiated. A stainless steel chromatographic column containing 10% by weight SE-30 packing and having dimensions of ⅛ inch diameter by 6 feet long was employed. Pyrolysis was conducted by energizing the probe at 10 amps for 15 seconds. The attenuation setting on the graph recorder for the chromatogram was XI while the attenuation setting for the pyrogram was X2. The left side of FIG. 3A illustrates the resulting chromatogram and the right side illustrates the resulting pyrogram.

EXAMPLE II

The procedure of Example I was repeated on a used silicone rubber seal made by the same manufacturer as the new rubber seal. The resulting chromatogram and pyrogram are illustrated, respectively, on the left and right sides of FIG. 3B.

Figure 3A:
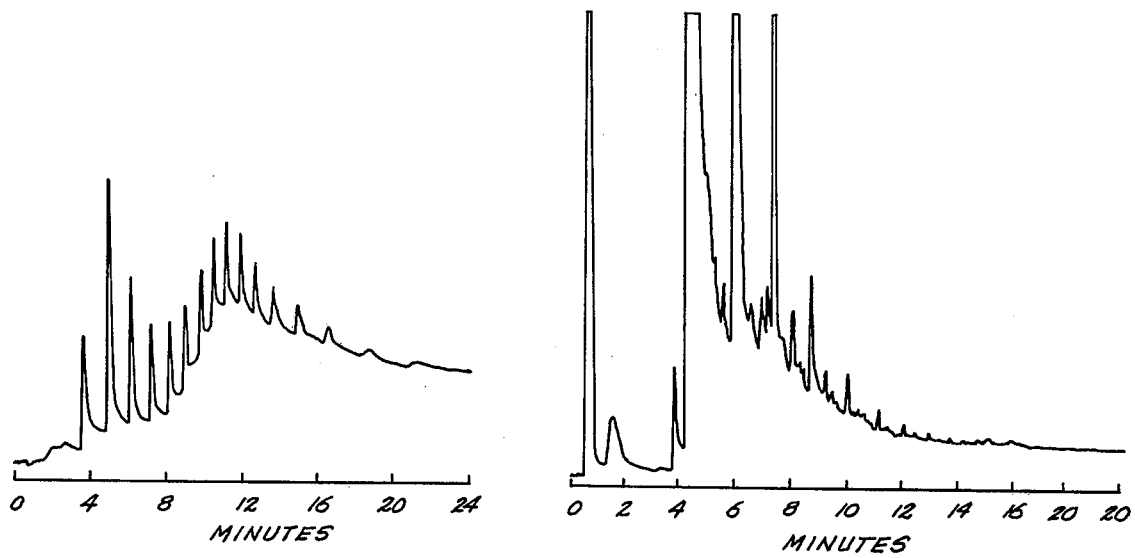
FIG. 3A is a chromatogram (left hand portion) and a pyrogram (right hand portion) of a sample of a silicone rubber seal prepared in accordance with the present invention.
Figure 3B:
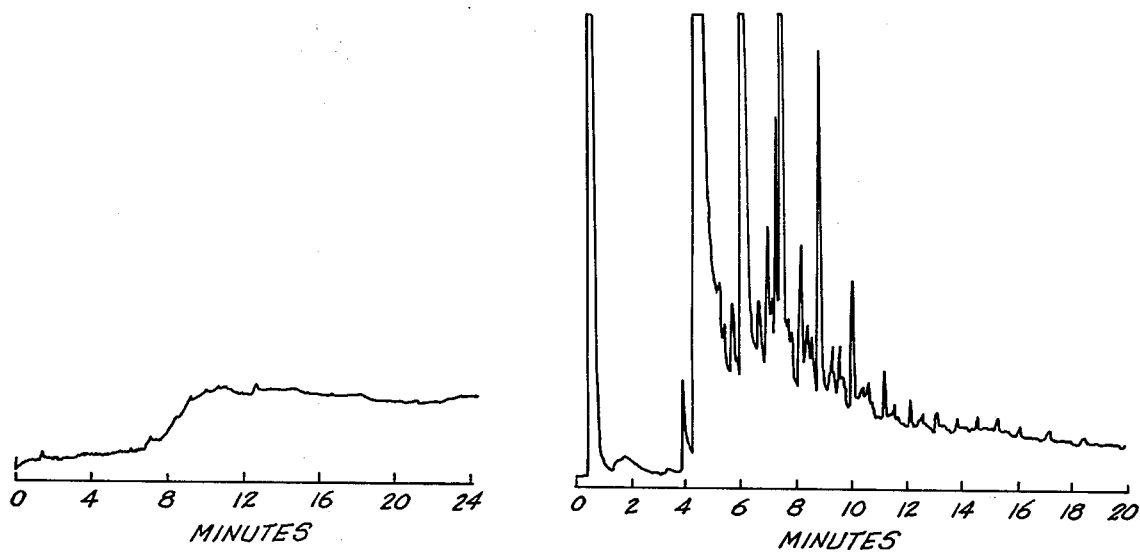
FIG. 3B is a chromatogram and a pyrogram of a used silicone rubber seal prepared in accordance with the present invention.

The y axis on each of FIGS. 3A and 3B represents graph recorder response while the x axis represents the time lapse. A comparison of the chromatograms of the left sides of FIGS. 3A and 3B shows completely different results, while the pyrograms on the right sides of FIGS. 3A and 3B are essentially identical. These results indicate that the volatile components of the used cavity seal were lost during its service life while the polymer components remained unchanged. The loss of volatile components in the used seal were causing it to crack and thus become unusable.

EXAMPLE III

An analysis of plasticized poly(vinyl chloride) tubing was conducted. The tubing was used as electrical insulation sleeving and conformed to government specification MIL-I-7444. The procedure was conducted with a chromatographic column containing 5% by weight SE-30 packing. The column was ⅛ inch in diameter by 6 feet long and of stainless steel construction. Pyrolysis was conducted by energizing the probe at 14 amps for 10 seconds. The attenuation setting on the graph recorder for the chromatogram was X16 while the setting for the pyrogram was X4. The resulting chromatogram (left side) and pyrogram (right side) are illustrated in FIG. 4A.

EXAMPLE IV

A second sample of the plasticized poly(vinyl chloride) tubing conformed to the government specification MIL-I-7444 except that it did not pass the required flammability test, although manufactured by the same supplier. The sample that did not pass the flammability test was analyzed in accordance with the procedure of Example III. The resulting chromatogram (left side) and pyrogram (right side) are illustrated in FIG. 4B.

Figure 4A:
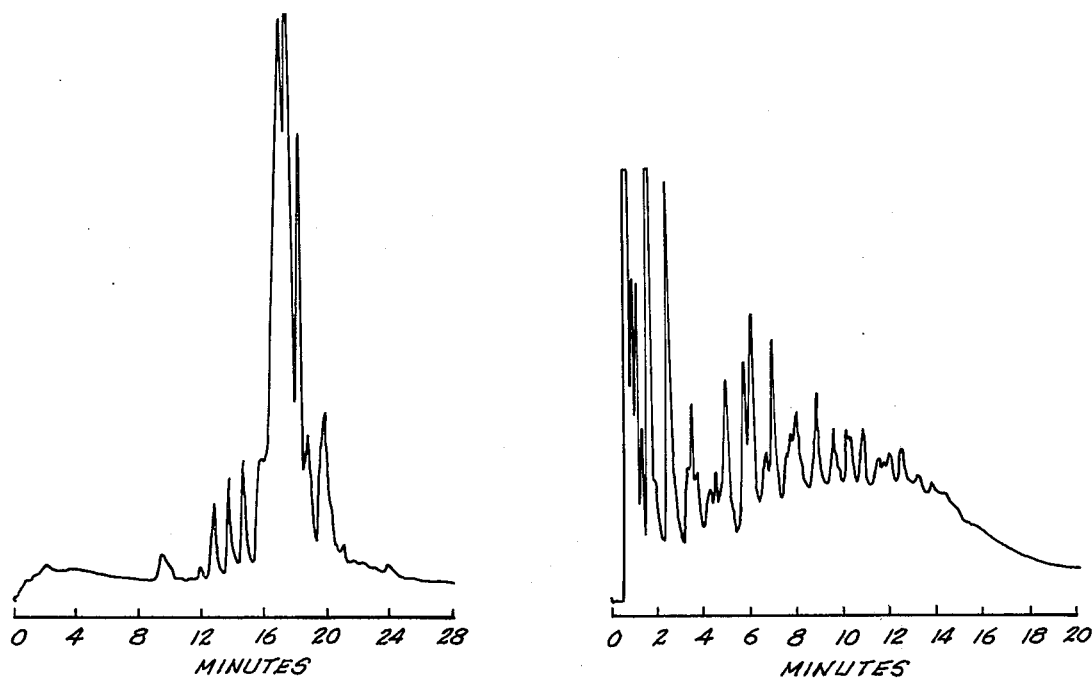
FIGS. 4A and 4B are chromatograms and pyrograms of two different poly(vinyl chloride) tubings prepared in accordance with the present invention.
Figure 4B:
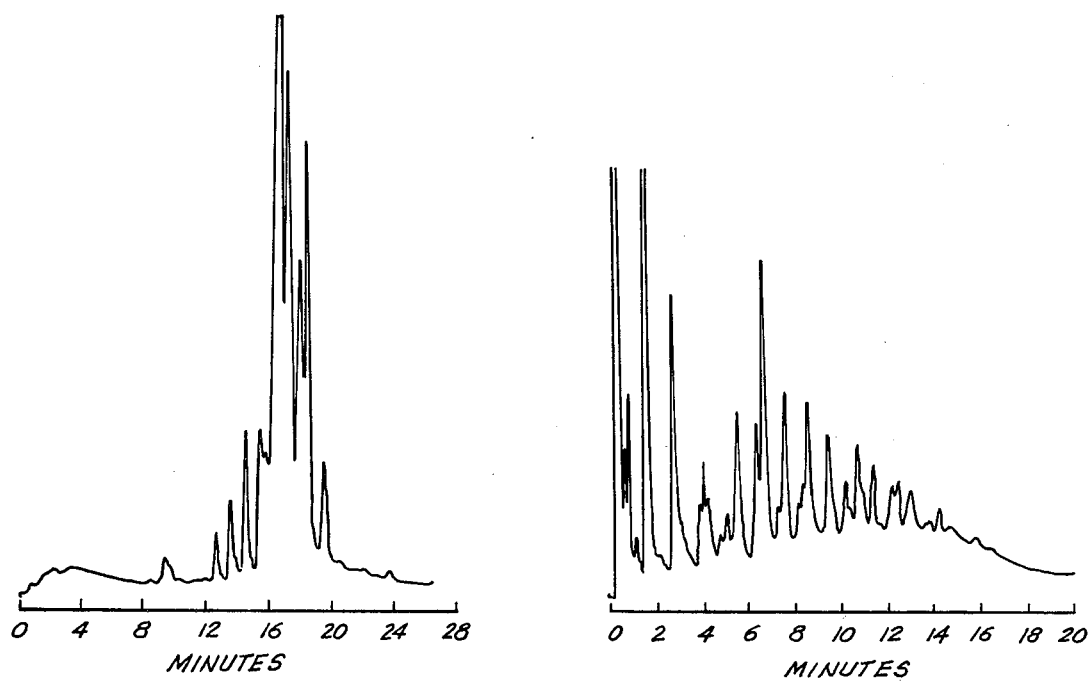

A comparison of the pyrograms of FIGS. 4A and 4B indicates that the nonvolatile high polymers are the same in both tubing samples analyzed in Examples III and IV. However, a comparison of the chromatograms of FIGS. 4A and 4B indicates that the volatile components of the samples of Examples III and IV are different. Furthermore, it is apparent from the chromatograms that the differences in the samples of Examples III and IV are not due to the incorporation of new components, but merely due to the different distribution of the same components. The similarity of the pyrograms eliminates doubt that a different polymer might have been accidentally used in the material analyzed in Example IV. The chromatograms and pyrograms therefore clearly show that during the manufacture of the material of FIG. 4B, either the degree of mixing was insufficient to produce a homogeneous product or weighing errors in the volatile components were made.

EXAMPLE V

A sample of nitrile rubber conforming to specification MIL-R-2765 was analyzed in accordance with the general procedure set forth above. The chromatographic column employed contained 10% by weight SE-30 packing and had a diameter of ⅛ inch and a length of 6 feet. The column was of stainless steel construction. Pyrolysis was carried out by energizing the pyrolysis probe at 14 amps for 5 seconds. The attenuation setting for both the chromatogram and the pyrogram was X16.

Figure 5A:
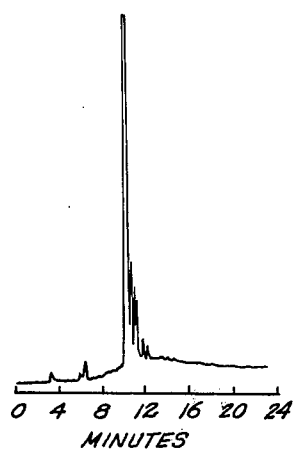
Figure 5A:
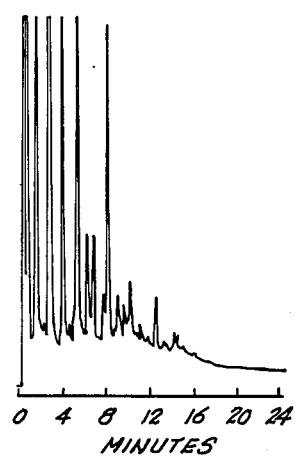

The resulting chromatogram and pyrogram are set forth on the left and right sides, respectively, of FIG. 5A.

EXAMPLE VI

The procedure of Example V was repeated on a second nitrile rubber conforming to specification MIL-R-6855, Class I, Grade 60. The resulting chromatogram (left side) and pyrogram (right side) are illustrated in FIG. 5B.

EXAMPLE VII

A sample of Paracril C was analyzed by the procedure of Example V with the exception that the chromatogram attenuation was set at X1 and the pyrogram attenuation was set at X4. Paracril C is a standard nitrile gum available from Uniroyal, Naugatuck, Conn. The resulting chromatogram (left side) and pyrogram (right side) are illustrated in FIG. 5C.

Figure 5B:
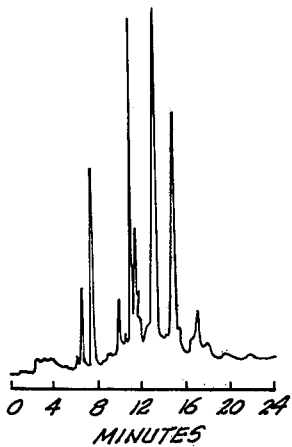
Figure 5B:
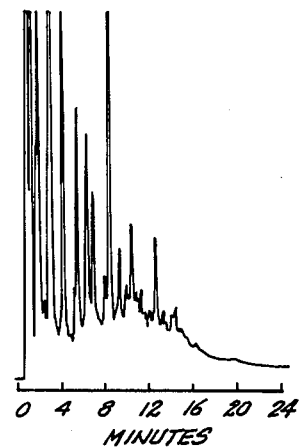
Figure 5C:
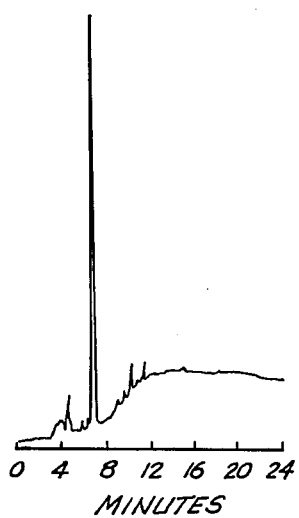
FIG. 5C is a chromatogram and pyrogram of a known nitrile gum, all of which were prepared in accordance with the present invention.
Figure 5C:
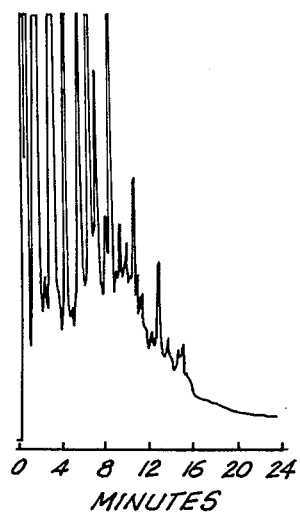

By a comparison of FIGS. 5A, 5B and 5C, it can be seen that the pyrograms are essentially identical, but that the chromatograms at the left side of the FIGURES are different, indicating a different formulation of volatile materials. If the sample material utilized to develop the pyrograms of FIGS. 5A and 5B were unknown, they could be identified as a nitrile rubber since the pyrogram of FIG. 5C is that of the known nitrile gum.

EXAMPLE VIII

A sample of butyl rubber meeting the specifications AMS 3237 (Aerospace Material Specification published by the Society of Automotive Engineers, Inc.) was analyzed in accordance with the general procedures set forth above. The chromatographic column contained 10% by weight SE-30 packing and had a diameter of ⅛ inch and a length of 6 feet. The column was constructed of stainless steel. The pyrolysis was conducted by energizing the probe with 12 amps for 15 seconds. The attenuation setting for both the chromatogram and the pyrogram was set at X2. The resulting chromatogram (left side) and pyrogram (right side) of Example VIII are set forth in FIG. 6A.

EXAMPLE IX

The procedure of Example VIII with the exception noted below was repeated on a second butyl rubber gum identified by the trademark BUTYL 101 and sold by Polysar, Inc., Akron, Ohio. The procedure of Example IX was identical to that of Example VIII with the exception that the attenuation setting for the chromatogram was X1 and the attenuation setting for the pyrogram was X4. The resulting chromatogram (left side) and pyrogram (right side) of Example IX are set forth in FIG. 6B.

Figure 6A:
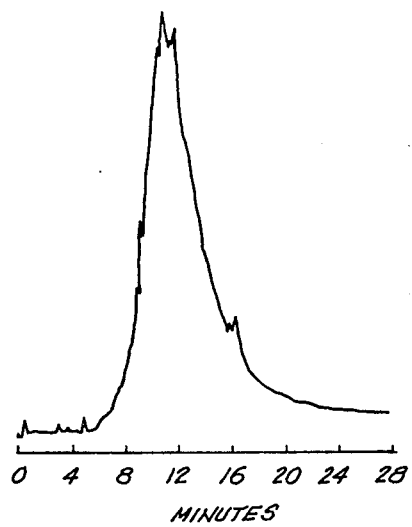
Figure 6A:
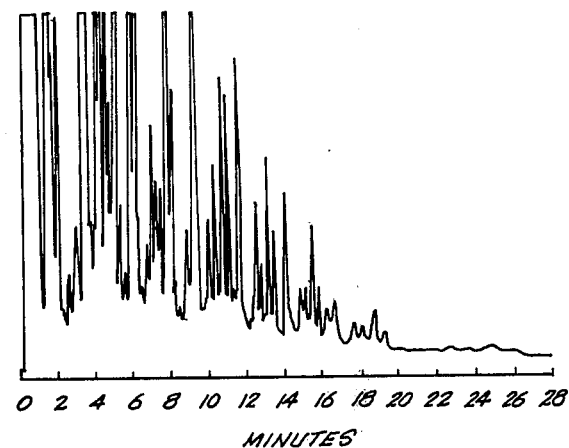
Figure 6B:
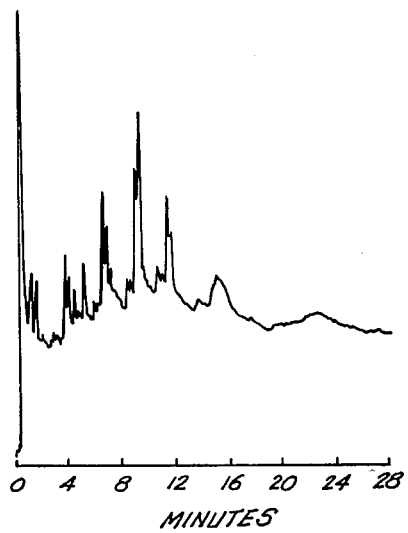
FIG. 6B is a chromatogram and a pyrogram of a known butyl gum, both of which were prepared in accordance with the present invention.
Figure 6B:
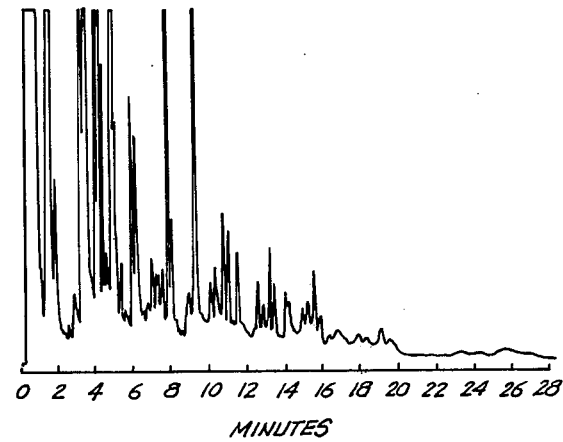

Polysar BUTYL 101 is a known butyl rubber gum. Note that the pyrogram of FIG. 6B is identical to that of FIG. 6A. Therefore, if the material of FIG. 6A were unknown, it could be identified as a butyl rubber. It is also to be noted that the volatile components of the AMS 3237 rubber are quite different from the volatile components in the Polysar BUTYL 101 rubber gum, an indication that the formulations of the two rubbers are different.

EXAMPLE X

Figure 7A:
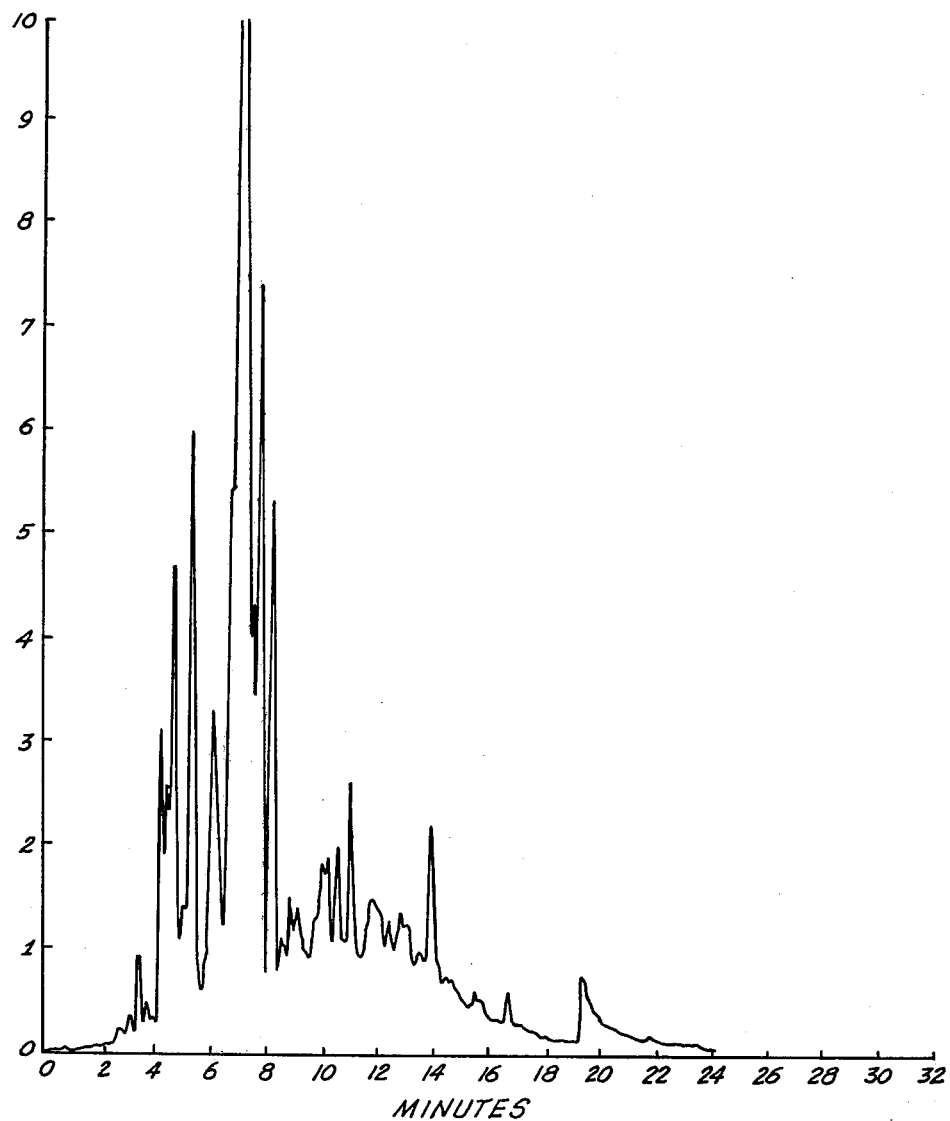
FIGS. 7A and 7B are a chromatogram and pyrogram, respectively, of an alkyd gloss enamel prepared in accordance with the present invention.
Figure 7B:
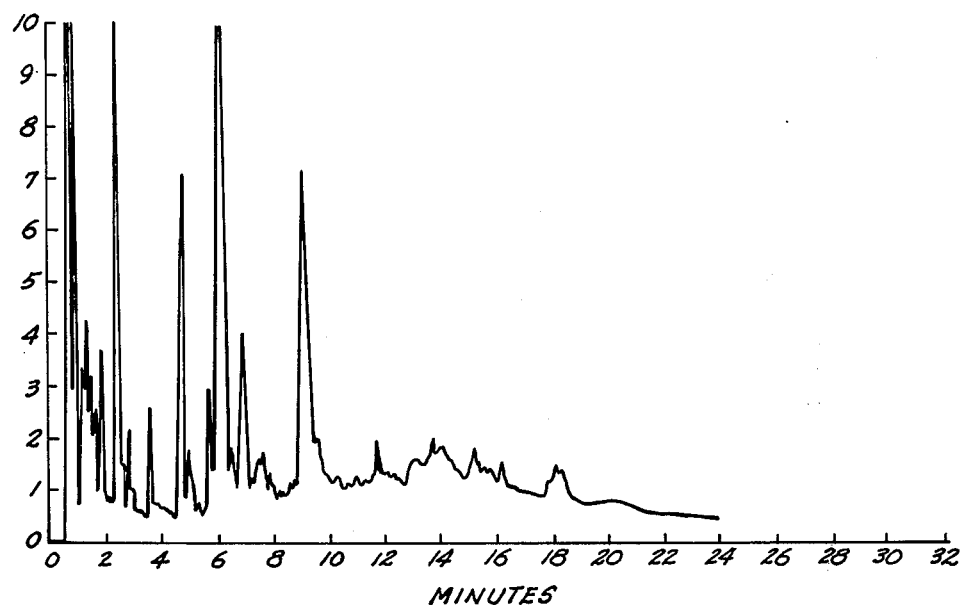

Materials other than rubbers can be analyzed in accordance with the broad procedures as set forth above. For example, paints such as alkyd enamels can be analyzed easily using the two step process of the present invention. For this example, a sample of a gloss alkyd enamel was analyzed. The enamel was identified as BMS 10-23D Type 1, orange yellow, Boeing Materials Specification, The Boeing Company, Seattle, Washington. The enamel is sold by Andrew Brown of Koppers Company and identified by product number A-2059-13538. The chromatographic column contained 5% by weight SE-30 packing and had a diameter of ⅛ inch and a length of 10 feet. The column was constructed of stainless steel. For the chromatogram, the column temperature was programmed from a beginning temperature of 30° C. to an ending temperature of 200° C. at a rate of 6° per minute. The temperature of the injection port and chamber was 270° C. The carrier gas, helium, was metered at a flow rate of 30 ml/minute. The attenuation setting on the graph recorder for the chromatogram was X6. For the pyrogram, the column was programmed for a temperature increase at a rate of 20° per minute from a starting temperature of 30° C. to an ending temperature of 300° C. The attenuation setting for the pyrogram was X16. Pyrolysis was conducted by energizing the probe at 12 amps for 15 seconds. Otherwise, the Operating Procedure set forth prior to Example I was followed. The resulting chromatogram is shown in FIG. 7A and the resulting pyrogram is illustrated in FIG. 7B.

Figure 8A:
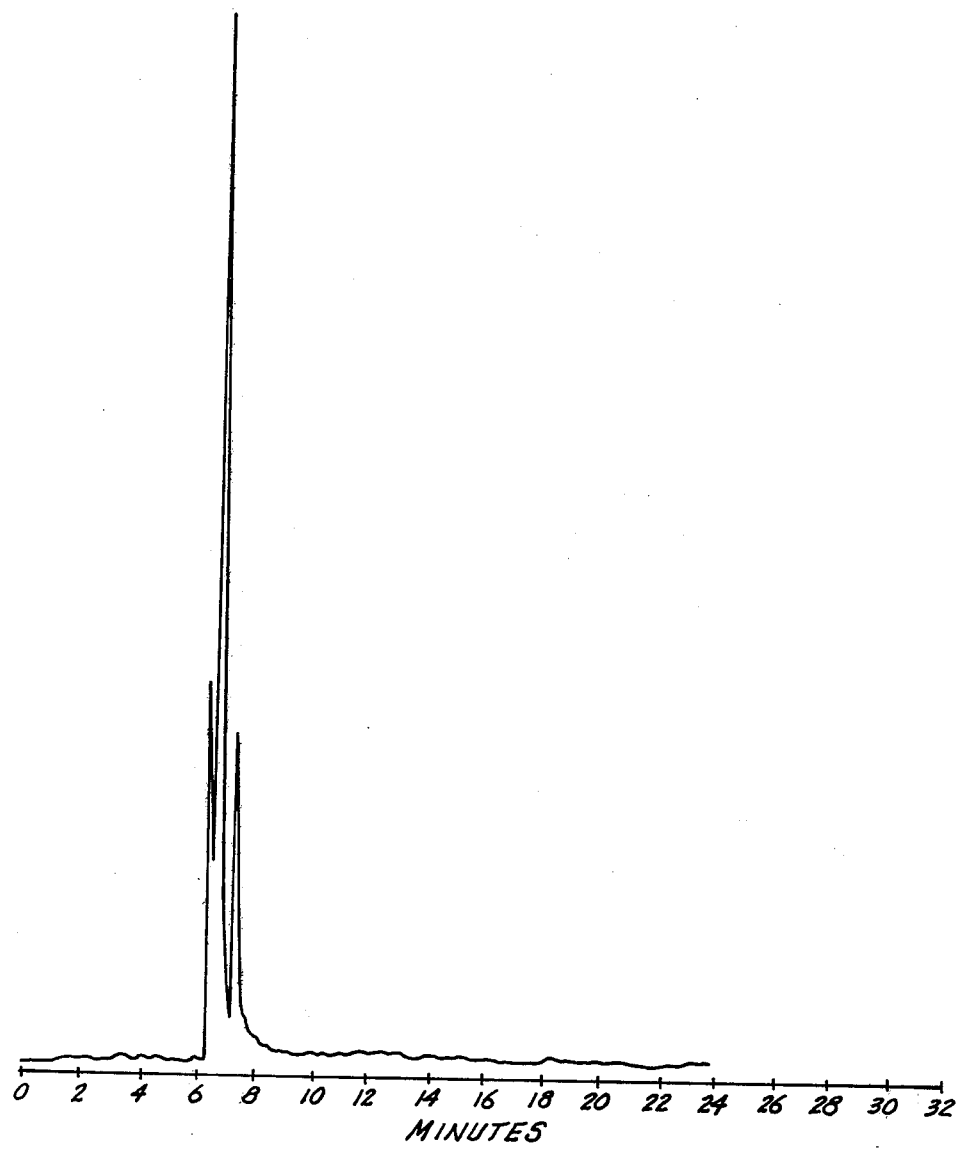
FIGS. 8A and 8B are a chromatogram and a pyrogram, respectively, of another alkyd gloss enamel prepared in accordance with the present invention.
Figure 8B:
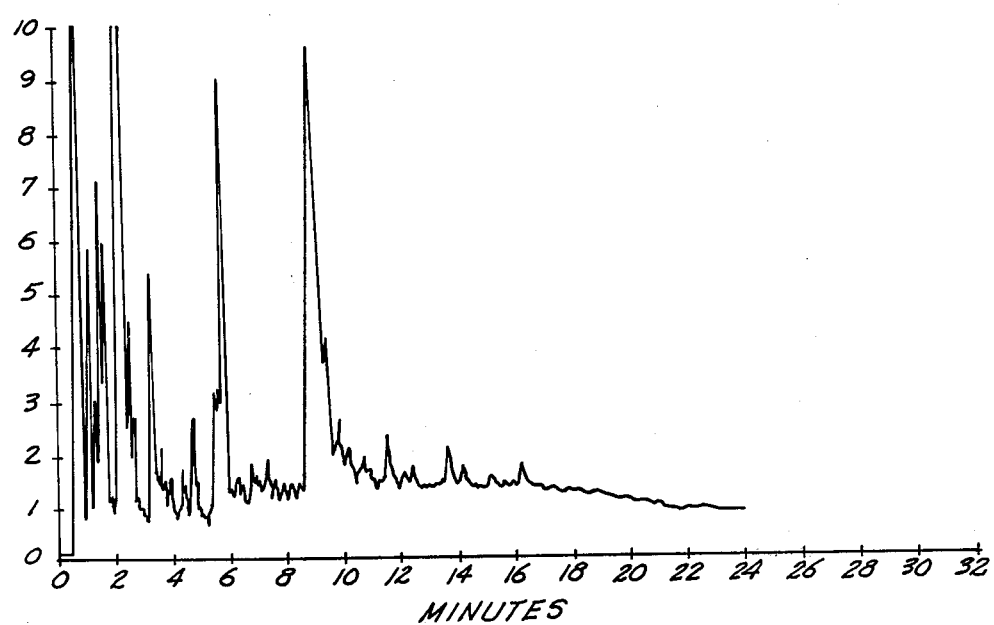

A similar alkyd enamel from a different source was analyzed in an identical manner. The resulting chromatogram and pyrogram are shown in FIGS. 8A and 8B, respectively. From the comparison of the pyrograms of FIGS. 7B and 8B, it was learned that both alkyd enamels contained the same nonvolatile materials. The two enamels varied widely in the solvents employed as can be clearly seen in the chromatograms of FIGS. 7A and 8A, which are indicative of the distinctive formulations of the two different enamels.

From the foregoing detailed description and Examples, it can be observed that the pyrolysis gas chromatography method of the present invention has distinct advantages over prior art analytic methods. For example, both the volatile and nonvolatile pyrolyzable components of materials can be analyzed while inserting the sample in the chromatographic apparatus only once. By contrast, the analysis of polymers containing volatile additives was accomplished in the prior art by separate processes: first extracting the volatile materials from the sample, analyzing the extracted sample, and then pyrolyzing the remainder of the sample in a gas chromatograph. The prior art extraction processes are time consuming and require large sample sizes. Moreover, the reproducibility of the prior art techniques is not as good. The approach of the present invention integrates the analysis of volatile and nonvolatile components into a single process. In the process of the present invention, no component of the original sample is lost and no foreign materials such as solvents and contaminants are added to the sample, thus providing a clean and reproducible fingerprint representative only of the components of the sample. Moreover, the chromatogram and pyrogram produced by the method of the present invention represent complete information on the sample, with the exception of any inorganic residue which may be left after pyrolysis.

The method of the present invention is particularly suitable for quality assurance in the manufacturing of compounded materials such as rubbers, flexible plastics, adhesives, organic coatings, and sealants. The performance of such materials depends not only on polymers but also on the proper proportions of volatile components including plasticizers and the exact dosage of other additives, which can critically alter the properties of these products. Variations in additives, solvents and plasticizers in different batches of such materials that can be ascertained in accordance with the present invention are, for example, demonstrated in FIGS. 4A and 4B. Thus, batch uniformity for quality assurance purposes can easily be checked by the methods of the present invention without interruption of the manufacturing process.

The method of the present invention is also useful for the purchaser who can assure a required quality of purchased material by monitoring formulation changes. Despite a requirement by the purchaser prohibiting formula changes in most material specifications, occasionally formulations of compounded materials are changed without notifying the purchaser. Very often, such changed formulations can still meet the specification requirement of mechanical properties of the purchaser, but may be unsatisfactory in other respects. The methods of the present invention can provide an easy and rapid method for monitoring formulation of purchased products to assure that there are no formulation changes. FIGS. 5A and 5B are examples of formulation differences in products purchased from two manufacturers. As previously pointed out, the chromatograms illustrated in FIGS. 5A and 5B are significantly different, and each represents a specific and different formulation from the other.

In accordance with another aspect of the present invention, a sample of oil or other viscous liquid can be introduced through the injection port and into the injection chamber of a chromatographic apparatus by employing a capillary tube having, for example, an internal diameter on the order of 0.2 to 0.8 mm. The oil is caused to flow into the capillary tube in a conventional manner from a source of material by simply touching the end of the capillary tube to the surface of the liquid. The sample size can then be very conveniently adjusted by contacting the end of the capillary with a piece of clean tissue paper, which withdraws a desired amount of liquid out of the capillary. The exact sample size can be measured with a ruler with the naked eye, under a microscope, or by weighing on a microbalance. After the sample of oil or other viscous liquid is placed in the capillary tube, the capillary tube is positioned inside the coil of a conventional spiral coil pyrolysis probe or other suitable sample holder. The spiral coil pyrolysis probe is conveniently employed because a conventional capillary tube can easily slide into and be retained by the spiral coil. The pyrolysis probe is utilized only as a convenient holder since pyrolysis is not employed in the gas chromatographic analysis that is described below.

Figure 9:
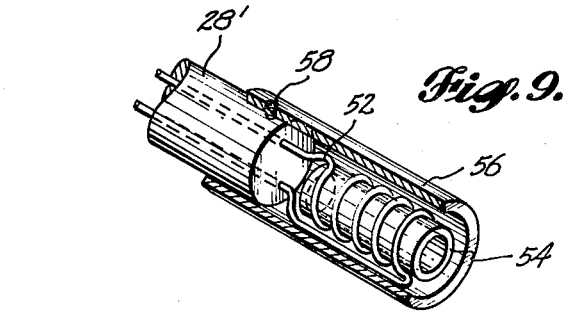
FIG. 9 is an enlarged isometric view of an alternative probe tip for pyrolysis and for use in inserting a viscous liquid sample into the injection chamber of a chromatographic apparatus in accordance with the present invention.
Figure 10:
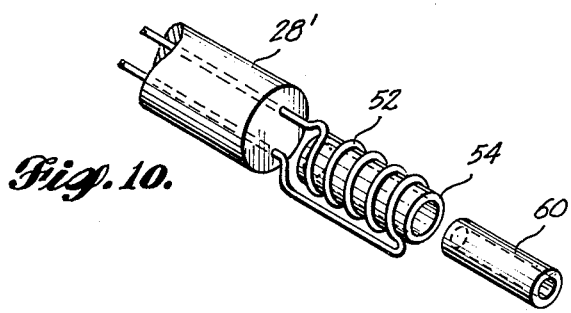
FIG. 10 is a modified embodiment of the apparatus of FIG. 9.

Referring to FIG. 9, the tip end of a spiral coil pyrolysis probe shank 28' carries a spiral coil 52. A glass capillary tube 54 containing a liquid sample (not shown) is inserted into the spiral coil and retained thereby. If desired, a sleeve 56 having an internal diameter slightly greater than the end of the probe shank 28' can be positioned around the spiral coil 52 to protect the coil while not in use. The sleeve 56 can be fastened to the end of the probe shank 28' by a suitable set screw 58 threadably engaging a suitable aperture in the sleeve. If it is desired to use a smaller diameter capillary tube for purposes of analyazing a smaller amount of material, a smaller internal diameter capillary tube 60 can be employed to carry the sample (see FIG. 10). The smaller diameter capillary tube 60 is then inserted into the larger capillary tube 54 held by the spiral coil 52.

Once the liquid is contained in the capillary tube and inserted into the coil of the spiral coil pyrolysis probe, the pyrolysis probe is inserted through the injection port into the injection chamber of a gas chromatographic apparatus in a manner identical to that described above in conjunction with the two step (volatilization and pyrolysis) process. First, however, the carrier gas and the injection chamber are heated to a predetermined high temperature at which the viscous liquid will be vaporized. It has been found that for most oils, a temperature on the order of from 50° C. to 400° C., and preferaby from 100° C. to 300° C., can be utilized. The temperature can be varied in accordance with the same considerations outlined above for volatile components in a sample containing both volatile and pyrolyzable components. As soon as the viscous liquid sample is inserted into the preheated injection chamber, the viscous liquid is vaporized and travels with the carrier gas to the chromatographic column. Thereafter, its separate components are differentially eluted from the column and analyzed by a flame ionization detector in a manner identical to that described above in conjunction with the two step process. A chromatogram is also printed in the identical manner.

To illustrate, the advantages and highly precise results obtained by introducing viscous liquid samples into a gas chromatographic apparatus in the manner just described can best be seen by a comparison of the method of the present invention with the prior art method of introducing a liquid by first placing the liquid in a syringe and thereafter inserting the needle of the syringe through a septum at the injection port and ejecting the contents of the syringe into the injection chamber.

EAXAMPLE XI

Figure 12:
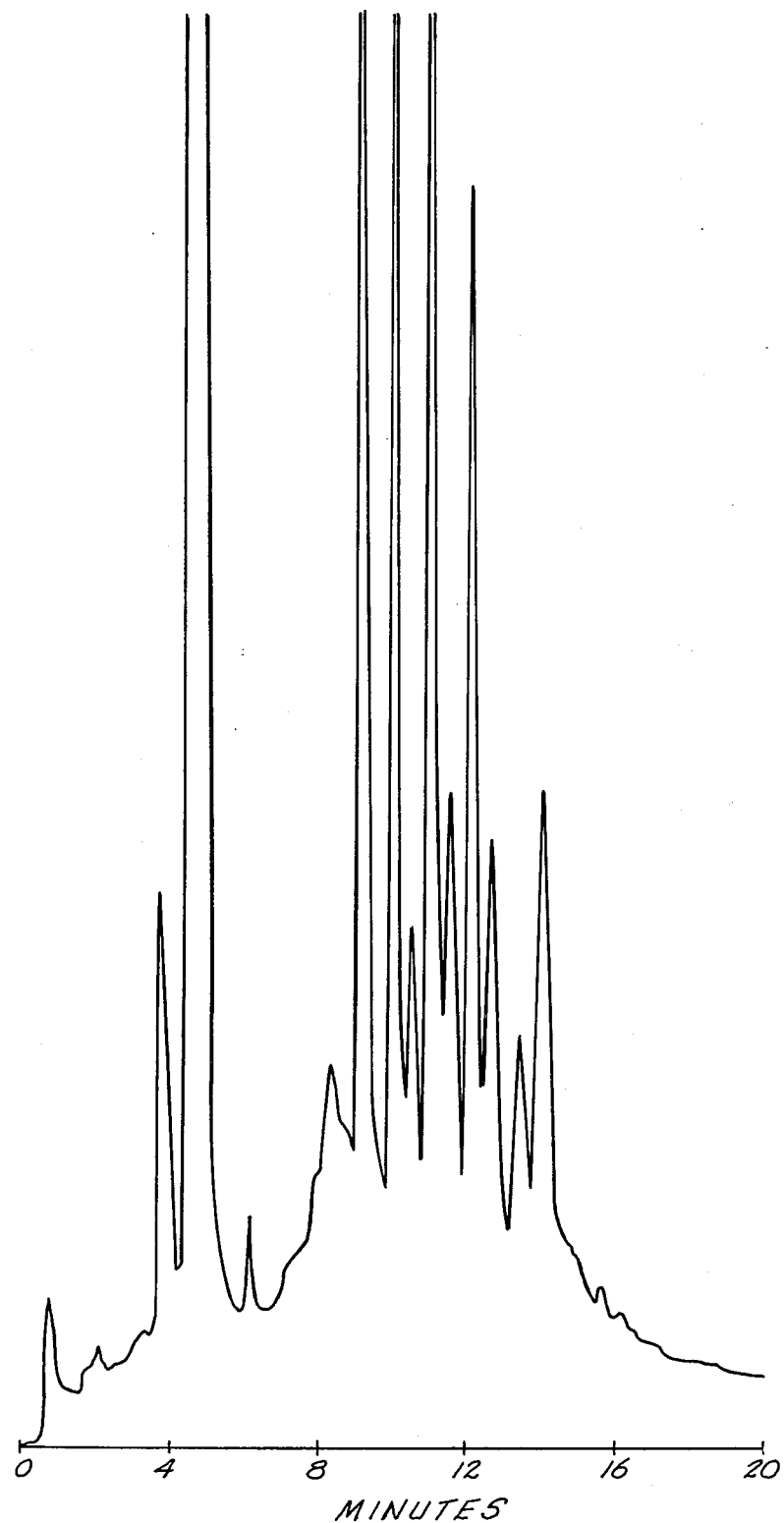
FIG. 12 is a chromatogram developed when the method of the present invention is utilized to insert a sample of the same viscous liquid into the injection chamber of a chromatographic apparatus.

A 1 microliter sample of oil was placed in a 3 mm section of a capillary tube having a length of approximately 12 mm and an internal diameter of 0.6 mm. The oil was a aircraft hydraulic fluid, sold under the tradename Hyjet IV by Chevron Company, San Francisco, Calif. The capillary tube was then inserted into the spiral coil of a pyrolysis probe. A gas chromatography apparatus identical to the utilized in conjunction with Examples I through X was employed to analyze the oil. The carrier gas and injection chamber were preheated to a temperature of 270° C. A stainless steel chromatographic column containing 5% by weight SE-30 packing was utilized. The column had a diameter of ⅛ inches and a length of 10 feet. The attenuation setting on the graph recorder was X2. The time at which the sample was inserted into the injection chamber was taken as zero time on the resulting chromatogram. The resulting chromatogram is illustrated in FIG. 12. By viewing FIG. 12, it can be seen that a great many volatile components are present in the oil. It can further be seen that sharp definition and separation between the components are obtained when the method of the present invention is employed.

EXAMPLE XII

Figure 11:
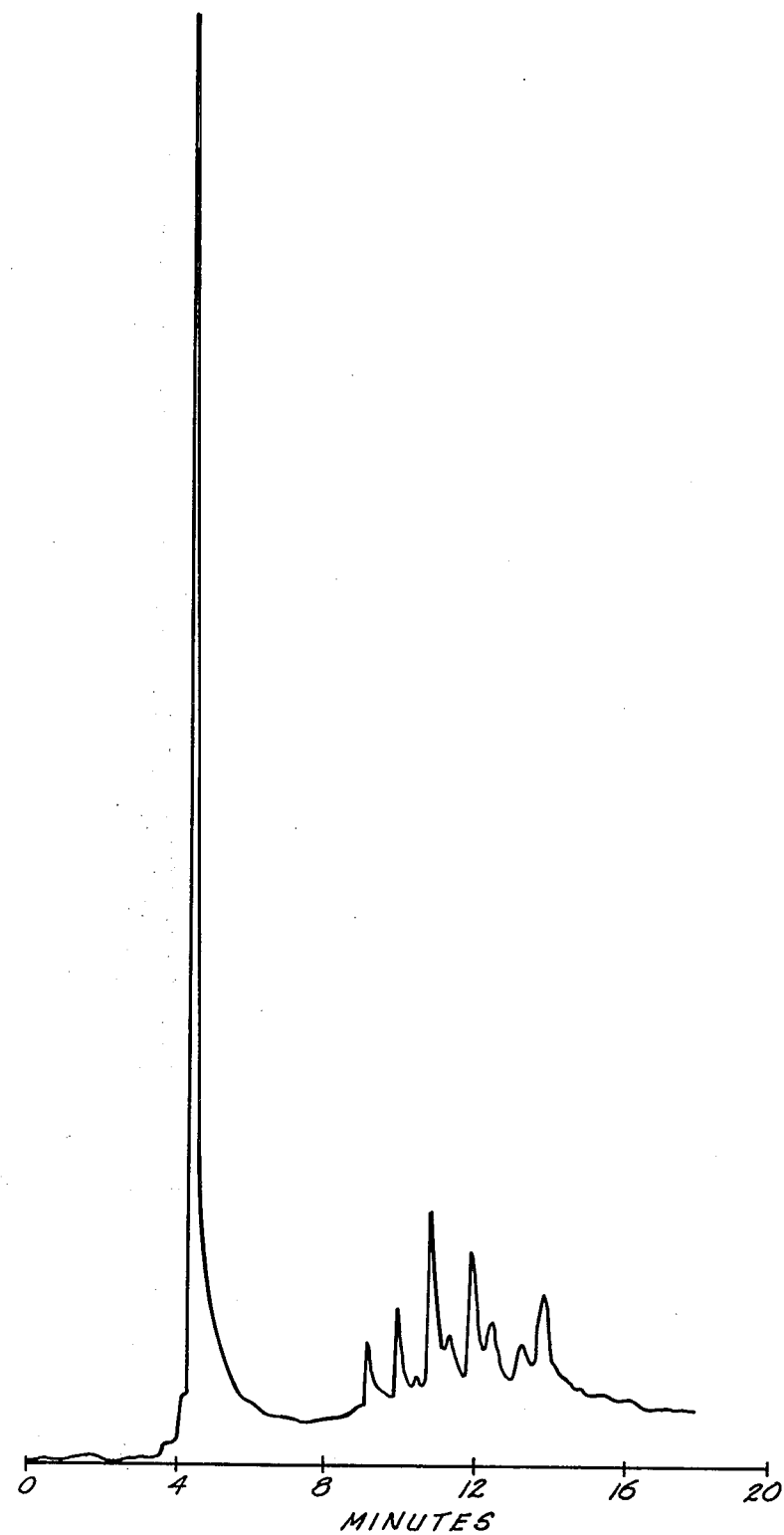
FIG. 11 is a chromatogram produced when a viscous liquid is injected by prior art means utilizing a syringe inserted through a septum in the injection port of a chromatographic apparatus.

The procedure of Example XI was repeated, with the exception that a 1 microliter sample of the same oil that was analyzed in Example XI was drawn into a conventional injection syringe and injected into the heated injection chamber. The needle of the syringe was inserted through a conventional septum covering the injection port and an attempt was made to eject all of the oil from the syringe. Since the oil was viscous, difficulty was encountered in forcing all of the oil from the syringe. As soon as the plunger on the syringe was pushed, the zero time on the chromatogram was begun. The resulting chromatogram via the prior art method is illustrated in FIG. 11.

As can be seen by a comparison of the chromatogram produced by the method of the present invention (FIG. 12) and the prior art chromatogram (FIG. 11), much better result is obtained by placing viscous liquid samples in a capillary tube, and inserting the tube into the injection chamber while maintaining the temperature of the carrier gas and the injection chamber at a level which will almost immediately vaporize the viscous liquid after its insertion into the chamber. To the contrary, the results obtained by the prior art method of syringe injection are unusable because only a fraction of the sample is eluted through the column, some sample leaked out, some sprayed on the injection chamber walls, and some stayed in the syringe, and because great difficulty is encountered in reproducing a chromatogram via the prior art methods.

The present invention has been described in conjunction with several embodiments. After reading the foregoing specification, one of ordinary skill will be able to effect various changes, substitutions of equivalents and other alterations without departing from the broad concept disclosed herein. It is therefore intended that the grant of Letters Patent hereon be limited only by the difinition contained in the appended claims and equivalents thereof.

The embodiments of the invention in which an exclusive property or privilege is claimed are defined as follows:

1. A method for separating and analyzing a sample containing at least one volatile component and at least one nonvolatile, pyrolyzable component comprising:
  establishing a flow of gaseous carrier fluid a sample injection chamber and thereafter through a chromatographic column,
  preheating the carrier gas flowing said injection chamber to a first predetermined temperature sufficiently high to vaporize said volatile component and below the pyrolysis temperature of said nonvolatile, pyrolyzable component,
  inserting said sample into said injection chamber while maintaining the temperature of said carrier gas passing through said chamber at said first predetermined temperature, allowing said volatile component to vaporize and pass through said chromatographic column with said carrier gas,
  after said volatile component has been vaporized from said sample and eluted from said column, heating said sample to a second predetermined temperature at which said nonvolatile component will be pyrolyzed to a gaseous reaction product, and
  allowing said reaction product to pass through said chromatographic column with said carrier gas.

2. The method of claim 1 further comprising:
  measuring the amount of said volatile component eluted from said column, and
  measuring the amount of said reaction product eluted from said column.

3. The method of claim 2 further comprising:
  graphically recording the amounts of said volatile component and said reaction product eluted from said column to form a graph characteristic of said sample.

4. The method of claim 1 wherein said sample is a polymer containing volatile matter and wherein said first predetermined temperature is in the range of 100° C. to 400° C.

5. The method of claim 4 wherein said first predetermined temperature is in the range of 250° C. to 300° C.

6. The method of claim 4 wherein said second predetermined temperature is in the range of 600° C. to 1500° C.

7. In a method for separating and analyzing a sample containing at least one volatile component and a pyrolyzable nonvolatile component wherein the sample is inserted into a carrier gas stream upstream of a chromatographic column, the improvement comprising:
  first vaporizing said volatile component of said sample in said carrier gas stream by preheating said carrier gas to a first predetermined temperature before contacting said sample with said carrier gas, said first predetermined temperature being sufficiently high to vaporize said volatile component and being below the pyrolysis temperature of said nonvolatile pyrolyzable component, and maintaining said carrier gas at said first predetermined temperature until substantially all of said volatile component of said sample is vaporized and is carried to said chromatographic column by said carrier gas, and
  thereafter pyrolyzing said nonvolatile component by heating said sample to a second predetermined temperature at which said nonvolatile component will react to form a gaseous pyrolysis product, and allowing said carrier gas to carry said gaseous pyrolysis product to said chromatographic column.

8. The method of claim 7 wherein said nonvolatile component is pyrolyzed after substantially all of said volatile component has been eluted from said chromatographic column.

9. The method of claim 7 further comprising:
  measuring the amount of said volatile component as it is eluted from said chromatographic column, and
  measuring the amount of said gaseous is pyrolysis product as it is eluted from said chromatographic column.

10. The method of claim 7 wherein said sample is a polymer and wherein said first predetermined temperature is in the range of 100° C. to 400° C.

11. The method of claim 10 wherein said first predetermined temperature is in the range of 250° C. to 300° C.

12. The method of claim 10 wherein said second predetermined temperature is at least about 600° C. to 1500° C.

13. A method for introducing a viscous liquid into a gas chromatographic column, said column having a sample chamber and an injection port, comprising the steps of:
  placing a sample of said liquid in a capillary tube, said sample being sufficiently large to fill a portion of said capillary tube,
  retentively positioning said capillary tube on a sample holder, establishing a flow of carrier gas through said sample chamber and through said gas chromatographic column, preheating said sample chamber and said carrier gas to a predetermined temperature, said predetermined temperature being sufficiently high to vaporize said viscous liquid and being lower than the temperature at which said viscous liquid pyrolyzes, inserting said sample holder including said capillary tube and said viscous liquid sample through said injection port into said sample chamber, such that said carrier gas flows freely aroung said capillary tube, and sealing the region between said injection port and said sample holder.

14. The method of claim 13 wherein said liquid is an oil and said predetermined temperature is in the range of 50° C. to 400° C.

15. The method of claim 14 wherein said predetermined temperature is in the range of 100° C. to 300° C.

16. a method for separating the components of a viscous liquid comprising:

establishing a flow of a carrier gas through a sample injection chamber and thereafter through a gas chromatographic column, preheating said carrier gas flowing through said sample injection chamber and through said chromatographic column to a predetermined temperature, said predetermined temperature being sufficiently high to vaporize said viscous liquid and being lower than the temperature at which said viscous liquid pyrolyzes, placing a sample of said liquid in a capillary tube, said sample being sufficiently large to fill a portion of said capillary tube, retentively positioning said capillary tube on the end of a sample holder, inserting said sample holder into said sample injection chamber and thereby positioning said capillary tube in said chamber such that said carrier gas flows at said predetermined temperature through said chamber and around said capillary tube, thereby vaporizing said liquid sample and carrying the vaporized components of said sample through said chromatographic column in a gaseous state.

17. The method of claim 16 wherein said predetermined temperature is in the range of from 50° C. to 400° C. and wherein said liquid comprises an oil.

18. The method of claim 17 wherein said predetermined temperature is in the range of 100° C. to 300° C.

19. The method of claim 16 further comprising:

measuring the amount of each vaporized component of said liquid sample as it is eluted in a gaseous state from said chromatographic column.

20. The methods of claims 13, 16 or 19 wherein said sample of said liquid placed in said capillary tube comprises a predetermined amount of said liquid.

* * * * *